United States Patent

Jung et al.

Patent Number: 5,332,849
Date of Patent: Jul. 26, 1994

[54] TRIS(SILYL) ALKANES AND THEIR PREPARATION METHODS

[75] Inventors: Il N. Jung, Seoul; Seung H. Yeon, Kyungki; Joon S. Han, Seoul, all of Rep. of Korea

[73] Assignee: Korea Institute of Science and Technology, Seoul, Rep. of Korea

[21] Appl. No.: 176,442

[22] Filed: Jan. 3, 1994

[51] Int. Cl.$^5$ .............................................. C07F 7/08
[52] U.S. Cl. ............................................... 556/435
[58] Field of Search ........................................ 556/435

[56] References Cited

U.S. PATENT DOCUMENTS

| | | | |
|---|---|---|---|
| 2,740,802 | 4/1956 | Wagner et al. | 556/435 |
| 4,778,908 | 10/1988 | Pillot et al. | 556/435 |
| 4,788,312 | 11/1988 | Paciorek et al. | 556/435 |
| 5,233,069 | 8/1993 | Jung et al. | 556/435 |
| 5,235,083 | 8/1993 | Jung et al. | 556/435 |

Primary Examiner—Paul F. Shaver
Attorney, Agent, or Firm—Oblon, Spivak, McClelland, Maier & Neustadt

[57] ABSTRACT

The present invention relates to a process for preparing tris(silyl)alkanes comprising directly reaction a mixture of organic compounds having a trichloromethyl group represented by formula I and hydrogen chloride or alkyl chlorides represented by formula II, with metallic silicon to give the tris(silyl)alkanes represented by formula III, IV, V and VI:

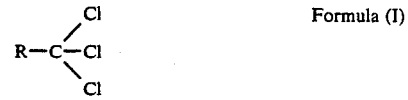

Formula (I)

R'Cl  Formula (II)

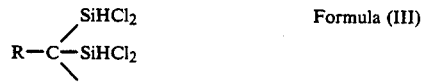

Formula (III)

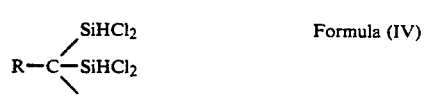

Formula (IV)

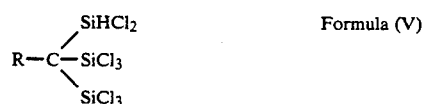

Formula (V)

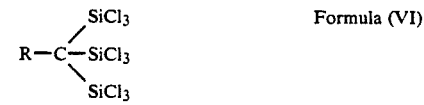

Formula (VI)

wherein R represent independently hydrogen or methyl and R' represents hydrogen, alkyl($C_1$-$C_4$), or $CH_2CH_2Cl$.

16 Claims, No Drawings

TRIS(SILYL) ALKANES AND THEIR PREPARATION METHODS

FIELD OF THE INVENTION

The present invention relates to tris(silyl)alkanes represented by formula (III), (IV), (V) and (VI), and a process for preparing the compounds comprising directly reacting a mixture of organic compounds having a trichloromethyl group represented by formula I and hydrogen chloride or alkyl chlorides represented by formula II, with metallic silicon to give the tris(silyl)alkanes having three dichlorosilyl groups (formula III), the tris(silyl)alkanes having two dichlorosilyl groups and one trichlorosilyl group (formula IV), the tris(silyl)alkanes having one dichlorosilyl groups and two trichlorosilyl groups (formula V), and the tris (silyl)alkanes having three trichlorosilyl groups (formula VI) in moderately high yields in the presence of copper catalyst at a temperature from 250° C. to 350° C. The different major product is obtained depending upon the alkyl chloride incorporated. n-Butyl chloride, t-butyl chloride, and propyl chloride gave tris(silyl)alkanes with one hydrogen substituted on each of the three silicon atoms represented by formula (III) as the major product. When 1,2-dichloroethane is incorporated, tris(silyl)alkanes having trichlorosilyl group represented by formula (VI) is the only major product.

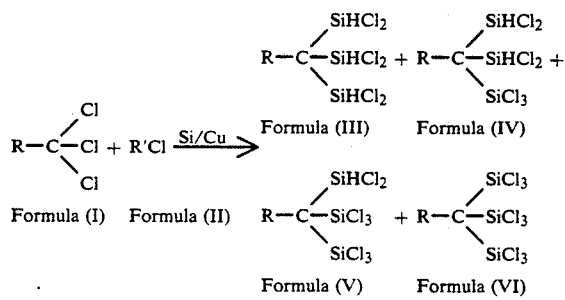

wherein R represent independently hydrogen or methyl and R' represents hydrogen, alkyl($C_1$-$C_4$), or $CH_2CH_2Cl$.

DESCRIPTION OF THE PRIOR ART

Methylchlorosilanes are the most important starting materials for silicones. E. G. Rochow discovered the direct process for the synthesis of methylchlorosilanes, reacting elemental silicon with methyl chloride in the presence of a catalyst in 1940 (E. G. Rochow U.S. Pat. No. 2,380,995).

$$Si + 2CH_3Cl \rightarrow (CH_3)_2SiCl_2$$

The reaction gives dimethyldichlorosilane, methyltrichlorosilane, trimethylchlorosilane, and tetrachlorosilane. A number of high boiling compounds are also found in the mixture of the products in a small quantity. The reaction rate and the nature of products depend on a large number of factors. These determining factors include the nature of the starting materials, the catalyst, the reaction temperature, the reaction pressure, the type of reactor used, and the degree of conversion of silicon and methyl chloride.

The catalyst for the direct process is always copper, in some cases cocatalysts such as zinc, aluminum, cadmium etc. are added. The co-catalysts enhance the reactivity of silicon metal and shorten the induction period and increase the selectivity of dimethyldichlorosilane production. The reaction is carried out at 250°–350° C., and the yield of dimethyldichlorosilane decreases at tempeatures above 300°. In the absence of a catalyst, the reaction is sluggish and gives irreproducible results (E. G. Rochow, J. Am. Chem. Soc., 67,963 (1945)). The composition of the products depends on the amount of copper used. The greater amount of copper is used, the higher is the chlorine content of the resulting products. The greatest catalytic efficiency is obtained when the amount of copper is 10% of the amount of silicon.

The reactivity of the silicon-copper mixture is connected with the formation of an intermetallic η-phase ($Cu_3Si$). The presence of the η-phase in the mixture is of fundamental importance for the selective synthesis of dimethyldichlorosilane (V. S. Fikhtengolts and A. L. Klebanskii, J. Gen, Chem. U.S.S.R., 27,2535 (1957)). It is known that the mixture of silicon powder and copper powder is heated 800° C. to 1000° C. in nitrogen, or better in hydrogen, the powders become sintered and the η-phase is formed (P. Trambouze, and B. Imelik, J. Chim. Phys., 51,505 (1954)). The η-phase is also chemically prepared by heating cuprous chloride with silicon at the temperature above 350° C. (R. J. H. Voorhoeve and J. C. Vlugter, J. Catalysis, 4,129 (1965)).

$$nSi + CuCl \rightarrow SiCl_4 + Cu_3Si + Cu + (n-2)Si$$

The reaction rate and the composition of the products in the direct process are highly temperature-dependent (A. L. Klebam skii and V. S. Fikhtengolts, J. Gen. Chem. U.S.S.R., 27, 2693 (1957)). It is much important to maintain the reaction temperature at an accurately specified temperature and to prevent any hot spot developing in the agglomerates of the solid phase. It is reported that at higher temperatures, the deposition of carbon on the surface of the metal mixture occur which slows down the reaction (J. C. Vlugter, and R. J. H. Voorhoeve, Conf. Accad. Lin cei, Alta Tech. Chim. 1961 p. 81 (1962)). This is why the reactor for the direct synthesis of methylchlorosilane must have a high thermal stability and an efficient heat transfer.

The direct process can be carried out in fixed bed, in stirred bed, and also in fluidized bed reactors. The process with the stirred bed reactors has the advantages over the fixed bed operation that the heat of reaction can be removed more easily and the movement of the powders causes fresh surface to be continuously exposed. Sellers and Davis reported that a mechanically stirred fluidized bed could be used (J. E. Sellers and J. L. Davis, U.S. Pat. No. 2,449,821). The metal powder was agitated in an up and down motion in a vertical reactor by means of spiral band rotated by a central shaft while a stream of methylchloride was up-ward through it. Bluestrim used a fluidized bed reactor for the production of methylchlorosilane (B. A. Bluestein, U.S. Pat. No. 2,887,502).

Petrov et al reported the preparations of chlorosilaalkanes by reacting silicon metal with α-dichloromethylsilanes. The reaction of α-dichloromethylsilanes with silicon metal at 360° C. gave 14% yield of tris(trichlorosilyl)methane and about 70% by-products due to the decomposition of the starting material (A. D. Petrov, S. I. Sahykh-Zade, E. A. Chernyshev. V. F. Mironov, Zh. Obschch. Khim., 26, 1248 (1956)). The expected tetrakis(silyl)methane was not obtained when bis (trichlorosilyl)dichloromethane was reacted with metallic silicon. All the products obtained were from the secondary reaction between metallic silicon and the compounds produced from the decomposition of bis(trichlorosilyl) dichloromethane. Several year later, Muller and his co-workers also studied the same reaction and reported that tetrakis(silyl)methane was not produced but the starting material decomposed (R. Muller and H. Beyer, Chem. Ber., 92, 1957 (1959); 96, 2894 (1963)).

We reported that trisilaalkanes as the major products and bis(silyl)methanes as the minor products were prepared as the minor products by reacting α-chloromethylsilanes with metallic silicon in the presence of copper catalyst at a temperature from 250° C. to 350° C. The copper catalyst was used 1-20% of total contact mixture, but the preferred amount was 5-10%. The reaction could be carried out in a fluidized bed or in a stirred bed reactor. Addition of micro-spherical acid clay to silicon metal improved the fluidization and gave better results (I. N. Jung, G. H. Lee, S. H. Yeon, M. Sku, U.S. Pat. No. 5,075,477 (1991. 12. 24)).

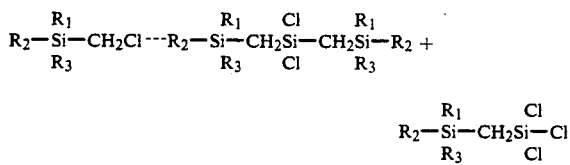

where $R_1$, $R_2$, and $R_3$ may independently be chloride or methyl.

We also reported that the direct synthesis of Si-H containing bis(silyl)methanes by reacting silicon metal with a mixture of α-chloromethylsilanes and hydrogen chloride. The bis(silyl)methane containing dichlorosilyl group was obtained as the major product and bis(silyl)methane containing trchlorosilyl group was obtained as the minor product. The major product could be explained by the reaction of the same silicon atom with each mole of two starting materials. The results suggest that the reactivities of the two starting materials were not much different. The major portion of the other by-products was trichlorosilane and tetrachlorosilane which were produced from the reaction between silicon metal and hydrogen chloride. The same results were obtained when hydrogen chloride was substituted by alkyl chlorides such as 1,2-dichloroethane, propyl chloride, n-butyl chloride, or t-butyl chloride, because alkyl chlorides decomposed to give off hydrogen chloride (U.S. patent application Ser. No. 07/965,705 (92. 12. 23)).

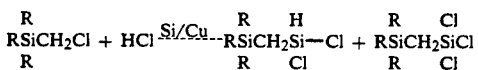

wherein $R_1$, $R_2$ and $R_3$ may independently be chloride or methyl.

We also found that bis(silyl)methanes having two dichlorosilyl groups at the both ends of the molecule along with bis(silyl)methane having two trichlorosilyl groups at the both ends and bis(silyl)methane having one dichlosilyl groups at the both ends and bis(silyl)methane having one dichlosilyl group and one trichlorosilyl group at each end were obtained by reacting a mixture of methylene chloride and hydrogen chloride (Korean Patent Appln. No. 92-935 (92. 1. 23)).

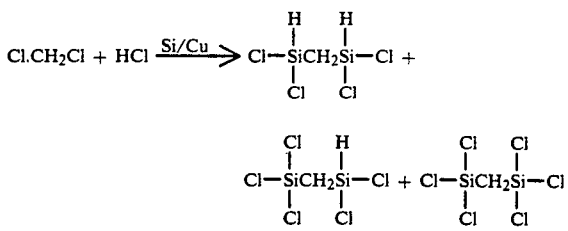

We also reported a process for preparing tris(silyl)methanes by directly reacting a mixture of α,α-dichloromethylsilanes and hydrogen chloride or alkyl chlorides with metallic silicon to give tris(silyl)methanes having two dichlorosily groups and the tris(silyl)methanes having one trichlorosilyl group and one dichlorosilyl group in moderately high yields in the presence of copper catalyst at a temperature from 250° C. to 350° C. The different major product is obtained depending upon the alkyl chloride incorporated. n-Butyl chloride, t-butyl chloride, and propyl chloride gave tris(silyl)methanes with one hydrogen substituted on each of the two silicon atoms as the major product. When 1,2-dichloroethane is incorporated, tris(silyl)methanes having two trichlorosilyl group is only the major product (Korean Patent Appln. No. 92-10293 (92. 6. 13)).

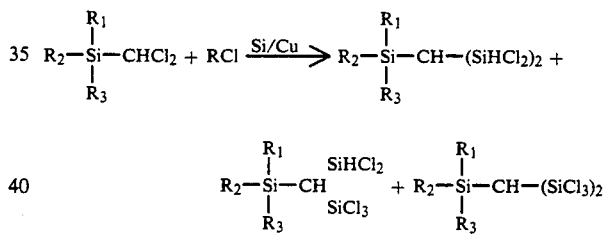

Wherein R represents hydrogen, alkyl($C_1$-$C_4$), or $CH_2CH_2Cl$, and $R_1$, $R_2$, and $R_3$ represent independently hydrogen or chloride.

SUMMARY OF THE INVENTION

The present invention relates to a process for preparing tris(silyl)alkanes by directly reacting a mixture of organic compounds having trichloromethyl groups represented by formula I and hydrogen chloride or alkyl chlorides represented by formula II, with metallic silicon to give the tris(silyl) alkanes represented by formula (III), (IV), (V) and (VI) in moderately high yields in the presence of copper catalyst at a temperature from 250° C. to 350° C. The different major product is obtained depending upon the alkyl chloride incorporated. n-Butyl chloride, t-butyl chloride, and propyl chloride gave tris(silyl)alkanes with one hydrogen substituted on each of the three silicon atoms represented in formula (III) as the major product. When 1,2-dichloroethane is incorporated, tris (silyl)alkanes having trichlorosilyl groups represented in formula (VI) is the only major product.

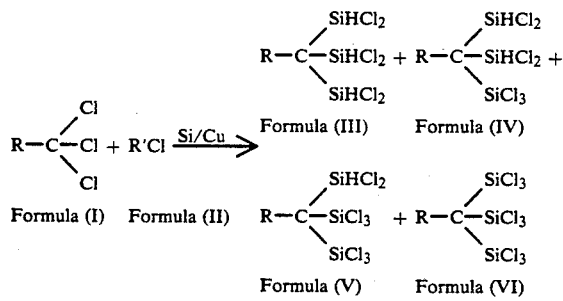

Wherein R represent independently hydrogen or methyl and R' represents hydrogen, alkyl($C_1$-$C_4$), or $CH_2CH_2Cl$.

The trichloroalkanes represented by formula I may be blended with hydrogen chloride or alkyl chloride before they are introduced to the reactor. They can be mixed in gaseous state after they are vaporized or in liquid state when formula II compound is a liquid. Although formula I compound may be mixed with formula II compound in all proportions by weight or by volume, the actual amount of formula II used will depend upon the desired ratio of hydrocarbon groups to chlorine atoms in the product. Thus, formula II may advantage ously use from about 0.1 to 12 moles per mole of formula I employed, the preferred ratio is 4.5 to 9 moles.

The reaction can be carried out in a fluid bed or in a stirred bed reactor. In the fluidized bed reaction, the addition of inert nitrogen gas to the starting gases is recommended to improve the fluidization. This also helps to remove the high boiling products out of the reactor. Metallugical grade silicon was employed in the process of this invention, which contained higher than 95% silicon by weight. The preferred purity of silicon was higher than 98%. The particle size of the silicon was 1-200 micron, but 20-200 micron was used for the fluidized reaction. The reaction temperature was from 200° C. to 360° C. The preferred reaction temperature range was 260°-320° C. The pressure at which the reaction of present invention is conducted is not critical and may be varied from 1 to 5 atmospheres, preferably 1 to 3 atmospheres. Addition of micro-spherical acid clay to silicon metal improved the fluidization and gave better results.

The commercially available copper catalysts for the reaction between silicon and methyl chloride are also found to be good catalysts for these reactions. The content of copper catalyst is 1-20% of total contact mass. The preferred copper content is 5-10%. The process in this invention is characterized to include promoters. The range of the promoters content is 0.001-2.0. The promoters include calcium, barium, zinc, tin, cadmium, manganese, magnesium, silver, and chromium, but are not limited to them.

The invention will be further illustrated by the following examples. It is, however, not intended that this invention will be limited by the examples.

EXAMPLE 1

Preparation of Si/Cu contact mixture (I-1)

After about 360 g (325-60 mesh) of silicon was mixed with 62.3 g of CuCl (10% of copper based on the weight of the silicon and copper) as a catalyst in order to provide a mixture, the mixture was contained in the reactor. Thereafter, the mixture was heated to a temperature ranging from 180° C. to 250° C. At this time, the agitator rotated at 60 rpm in order to mix the mixture completely together with blowing slowly dried nitrogen. When the temperature in the reactor was raised to about 370° C., the silicon reacted with the CuCl to form η-phase $Cu_3Si$, and $SiCl_4$ was obtained as a by-product which was removed from the reactor. In the case of using a promoter, 0.8 g of a promoter metal was added to the mixture after the reaction was completed.

EXAMPLE 2

Preparation of Si/Cu contact mixture (I-2-I-15)

In case of using metallic copper or copper catalysts which were used in the synthesis of methylchlorosilanes instead of the CuCl as described in EXAMPLE 1, 10% of the copper based on the weight of the silicon and copper was mixed with the silicon. The mixture was heated at 350° C. for 2 hours in the reactor together with blowing hydrogen chloride or methyl chloride in order to be activated.

The compositions of the contact mixtures prepared in Examples 1 and 2 are shown in Table 1.

TABLE 1

| | | Compositions of Si/Cu Contact Mixture | | | | |
|---|---|---|---|---|---|---|
| Sample No. | Si (g) | Cu Catalyst Form (g) | Promoter Metal (g) | | Metal (g) | Remark |
| I-1 | 360 | CuCl 62.3 | | | | |
| I-2 | 380 | Cu 20.0 | | | | |
| I-3 | 360 | Cu 40.0 | Cd | 2.0 | | |
| I-4 | 360 | Cu 40.0 | Zn | 2.0 | | |
| I-5 | 380 | Cu 20.0 | Cd | 2.0 | Sn 0.02 | |
| I-6 | 380 | Cu 20.0 | Ca | 2.0 | | |
| I-7 | 380 | Cu 20.0 | Ca | 2.0 | Cd 2.0 | |
| I-8 | 360 | Cu 40.0 | Ag | 2.0 | | |
| I-9 | 360 | Cu 40.0 | Ag | 2.0 | Cd 2.0 | |
| I-10 | 360 | Cu 40.0 | Mn | 2.0 | | |
| I-11 | 360 | Cu 40.0 | Mn | 2.0 | Cd 2.0 | Acid clay added |
| I-12 | 360 | Cu 40.0 | Mg | 2.0 | | |
| I-13 | 360 | Cu 40.0 | Mg | 2.0 | Cd 2.0 | |
| I-14 | 360 | Cu 40.0 | Cr | 2.0 | | Acid clay added |
| I-15 | 360 | Cu 40.0 | Cr | 2.0 | Cd 2.0 | |

EXAMPLE 3

Reaction of silicon with 1:6 mixture of chloroform and hydrogen chloride 402 g of Si/Cu contact mixture (I-3) prepared in EXAMPLE 2 was charged in an agitating-type reaction bath, and dry nitrogen gas was blown into the reactor at the rate of 200 ml/min. After increasing the temperature in the reactor up to 300° C., chloroform was pumped using a syringe pump at the rate of 10.0 ml/hr to the evaporator attached to the bottom of the reactor, while hydrogen chloride were also blown therein at the rate of 280 ml/min (mole ratio of chloroform and hydrogen chloride=1:6). 1 minute after the initiation of pumping, increase of the temperature caused by an exothermic nature of the reaction was observed and reaction products began to flow along the wall of an receiver flask. While maintaining the above conditions, reaction product was taken every hour.

The obtained reaction products were analyzed by using a gas chromatograph (packed column, 5% SE-54, 1.5 m×⅛" O.D., SS, TCD) and fractionally distilled to separate its constituents from one another, so that their structures could be determined. The structure of each constituent was determined by using a nuclear magnetic resonance spectroscopy and a mass spectrometry. After the reaction for 2 hours, 55.1 g of products was collected, while 29.4 g of chloroform was used.

The composition of the products contained 23.7 g (43.0%) of 1,1,3,3-tetrachloro-2-(dichlorosilyl)-1,3-disilapropane (formula III); [NMR(CDCl$_3$), δ 5.83 (s, 3H, Si—H), 1.56 (s, 1H, —CH═)] and 7.8 g (14.2%) of 1,1,1,3,3-pentachloro-2-(dichlorosilyl)-1,3-disilapropane (formula IV); [NMR(CDCl$_3$), δ 5.86 (s, 2H, Si-H), 1.83 (s, 1H, —CH═)], and 0.5 g (0.9%) of 1,1,1,3,3,3-hexachloro-2-(dichlorosilyl)-1,3-disilapropane (formula V); [NMR(CDCl$_3$), δ 5.89 (s, 1H, Si—H), 2.10 (s, 1H, —CH═)], and 0.2 g (0.4%) of 1,1,1,3,3,3-hexachloro-2-(trichlorosilyl)-1,3-disilapropane (formula VI); [NMR(CDCl$_3$), δ 2.37 (s, 1H, —CH═)]. 1,1,3,3-Tetrachloro-1,3-disilapropane (11.8%), 1,1,1,3,3-pentachloro-1,3-disilapropane (4.5%), and 1,1,1,3,3,3-hexachloro-1,3-disilapropane (1.3%) which were the products produced from the reaction of silicon with a mixture of methylene chloride and hydrogen chloride were also obtained. 23.9% of the other by-products contained trichlorosilane (18.7%) and unidentified substances.

The reaction was carried out under the same condition and by the same reactor as employed above, except that the reaction temperature varied from 260° C. to 340° C. The results obtained from the reactions are shown in Table 2.

EXAMPLE 4

Reaction of silicon with a mixture of chloroform and hydrogen chloride

The reaction was carried out at 260° C. under the same condition and by the same reactor as employed in EXAMPLE 3, except that the mixing ratio of chloroform and hydrogen chloride varied from 1:2 to 1:6. The results obtained from the reactions are shown in Table 3. The results shown in Entry No. 9 of Table 3 are obtained from the reaction in which 20.0 g (5% based on the weight of the silicon and copper) of acid clay was added to the contact mixture. The contact mixture was recharged after 20% conversion and results were about same.

TABLE 3

| | | | | | | | | | | |
|---|---|---|---|---|---|---|---|---|---|---|
| | | The mixing ratio of Reactants and Product Compositions | | | | | | | | |
| Entry | CHCl$_3$: | CHCl$_3$ | Rxn. | Amt. of | Composition of Product (%) | | | | | |
| No. | HCl | used (g) | Time (hr) | Products (g) | III | IV | V | VI | others | Remark |
| 6 | 1:4.5 | 29.4 | 2.0 | 51.6 | 38.9 | 15.7 | 0.9 | 0.6 | 43.9 | |
| 1 | 1:6 | 29.4 | 2.0 | 55.1 | 43.0 | 14.2 | 0.9 | 0.4 | 41.5 | |
| 7 | 1:9 | 29.4 | 2.0 | 59.7 | 37.4 | 9.7 | 0.6 | 0.4 | 51.9 | |
| 8 | 1:12 | 29.4 | 2.0 | 63.4 | 33.7 | 9.5 | 0.5 | 0.4 | 56.3 | |
| 9 | 1:6 | 29.4 | 2.0 | 54.6 | 43.3 | 14.7 | 1.0 | 0.4 | 40.6 | acid clay |

EXAMPLE 5

Reaction of various contact mixtures with a mixture of chloroform and hydrogen chloride The reaction was carried out under the same condition and by the same reactor as employed in Entry No. 3 of Example 3, except the different contact mixture was used. All the contact mixture listed in Table 1 have been tested and the results obtained from the reactions are shown in Table 4.

TABLE 2

| | | | | | | | | |
|---|---|---|---|---|---|---|---|---|
| | | Reaction Temperatures and Products Composition | | | | | | |
| Entry | Temp. | CHCl$_3$ | Rxn. | Amt. of | Composition of Product (%) | | | |
| No. | (°C.) | used (g) | Time (hr) | Products (g) | III | IV | V | VI | others |
| 1 | 260 | 29.4 | 2.0 | 55.1 | 43.0 | 14.2 | 0.9 | 0.4 | 41.5 |
| 2 | 280 | 29.4 | 2.0 | 56.2 | 38.7 | 16.8 | 2.8 | 2.5 | 39.2 |
| 3 | 300 | 29.4 | 2.0 | 52.9 | 34.0 | 19.0 | 2.2 | 1.6 | 43.2 |
| 4 | 320 | 29.4 | 2.0 | 42.1 | 24.8 | 18.2 | 4.2 | 2.6 | 50.2 |
| 5 | 340 | 29.4 | 2.0 | 40.2 | 22.4 | 19.3 | 6.3 | 3.2 | 48.8 |

TABLE 4

| | | | | | | | | | | |
|---|---|---|---|---|---|---|---|---|---|---|
| | | | Contact Mixtures and Product Compositions | | | | | | | |
| Entry | contact | CHCl$_3$ | Rxn. | Amt. of | Composition of Product (%) | | | | | |
| No. | mixture | used (g) | Time (hr) | Products (g) | III | IV | V | VI | others | Remark |
| 10 | I-1 | 29.4 | 2.0 | 50.8 | 5.2 | 10.8 | 11.4 | 5.4 | 67.2 | |
| 11 | I-2 | 29.4 | 2.0 | 54.4 | 7.3 | 13.5 | 8.5 | 4.7 | 66.0 | |
| 12 | I-4 | 29.4 | 2.0 | 43.9 | 18.6 | 17.3 | 5.8 | 1.5 | 56.8 | |
| 13 | I-5 | 29.4 | 2.0 | 52.6 | 8.2 | 9.3 | 20.4 | 12.8 | 49.3 | |
| 14 | I-6 | 29.4 | 2.0 | 53.8 | 5.4 | 6.3 | 18.7 | 10.5 | 59.1 | |
| 15 | I-7 | 29.4 | 2.0 | 53.1 | 11.3 | 14.2 | 12.1 | 3.2 | 59.2 | |
| 16 | I-8 | 29.4 | 2.0 | 53.4 | 5.8 | 7.6 | 22.9 | 13.7 | 50.0 | |
| 17 | I-9 | 29.4 | 2.0 | 51.3 | 21.5 | 17.6 | 8.4 | 4.5 | 48.0 | |
| 18 | I-10 | 29.4 | 2.0 | 49.3 | 6.9 | 8.4 | 18.4 | 11.8 | 54.5 | |
| 19 | I-11 | 29.4 | 2.0 | 52.5 | 23.8 | 16.3 | 9.1 | 5.2 | 45.6 | |
| 20 | I-12 | 29.4 | 2.0 | 50.9 | 5.7 | 8.8 | 21.0 | 12.1 | 52.4 | |
| 21 | I-13 | 29.4 | 2.0 | 53.0 | 7.4 | 14.3 | 8.2 | 5.3 | 64.8 | |
| 22 | I-14 | 29.4 | 2.0 | 51.7 | 5.5 | 7.5 | 19.3 | 13.4 | 54.3 | |
| 23 | I-15 | 29.4 | 2.0 | 53.2 | 24.5 | 15.9 | 8.2 | 4.1 | 47.3 | |

EXAMPLE 6

Reaction of silicon with a mixture of chloroform and alkyl chloride

The following experiment demonstrates Entry No. 24 of Table 5. the reaction was carried out at 260° C. under the same condition and by the samereactor as employed in Example 3, except that the same amount of t-butyl chloride was used as the hydrogen chloride source. 1:6 mixture of chloroform and t-butyl chloride was prepared by mixing 28.8 g (0.241 mole) of chloroform and 133.8 g (1.446 mole) of t-butyl chloride. The mixture was pumped at the rate of 67 ml/hr to the evaporator attached to the bottom of the reactor, while $N_2$ was also blown therein at the rate of 200 ml/min. After the reaction for 2 hours, 56.0 g of products was collected. The composition of the products contained 24.8% of formula III, 9.2% of formula IV, and 2.3% of formula V. The by-product contained 63.7% of trichlorosilane, and tetrachlorosilane. No starting material was recovered.

The reaction was carried out under the same condition and by the same reactor as employed above, except that the different mixing ratio and differnet kind of alkyl chloride were used. The gaseous by-product which was not trapped in the condenser was detected to be mostly isobutene produced from the decomposition of t-butyl chloride. n-Butyl chloride i-propyl chloride, or 1,2-dichloroethane was used instead of t-butyl chloride. In these cases, the gaseous by-product from the decomposition of alkyl chloride was 2-butene, propylene, or ethylene, respectively. When the half of the alkyl chloride was replaced by hydrogen chloride, the composition of the reaction products was about same as before. The results obtained from the reactions are shown in Table 5.

therein to improve the fluidization. After the reaction for 2 hours, 51.5 g of products was collected, while 29.4 g of chloroform was used. The same reaction was carried out using different hydrogen chloride sources but same 1:6 mixing ratio. The reaction conditions for Entry No. 31 were same as those for Entry No. 30 except that the pressure of the reactor was raised to 3 kg/cm$^2$. the results obtained from the reactions are shown in Table 6. More than 10% of the starting chloroform was recovered for all the reactions.

TABLE 6

Results of the Reaction using a Fluidized Bed Reactor

| Entry No. | R'Cl | CHCl$_3$ used (g) | Reaction Time (hr) | Amt. of Products (g) | Composition of Product (%) | | | | | starting material | Remark |
|---|---|---|---|---|---|---|---|---|---|---|---|
| | | | | | III | IV | V | VI | others | | |
| 28 | t—BuCl | 28.8 | 2.0 | 52.4 | 22.8 | 9.4 | 2.5 | 0.9 | 49.0 | 15.4 | |
| 29 | n—BuCl | 28.8 | 2.0 | 59.2 | 5.3 | 6.5 | 1.9 | 0.4 | 69.7 | 16.2 | |
| 30 | HCl | 29.4 | 2.0 | 51.5 | 29.8 | 8.7 | 2.4 | 0.8 | 46.0 | 12.3 | |
| 31 | HCl | 29.4 | 2.0 | 53.2 | 31.2 | 9.6 | 2.7 | 0.8 | 43.6 | 12.1 | 3 kg/cm$^2$ |

EXAMPLE 8

Reaction of silicon with a mixture of 1,1,1-trichloroethane and hydrogen chloride Si/Cu contact mixture (I-4) prepared in EXAMPLE 2 was reacted with a 1:6 mixture of 1,1,1-trichloroethane (35.6 g) and hydrogen chloride under the same condition as employed in EXAMPLE 3. After 2 hours reaction at 320° C., 58.3 g of products was obtained. The composition of the products contained 8.1 g (13.9%) of 1,1,3,3-tetrachloro-2-(dichlorosilyl)-2-methyl-1,3-disilapropane (formula III); [NMR(CDCl$_3$); δ 5.73 (s, 3H, Si-H), 1.66 (s, 3H, —CH$_3$)], 4.5 g (7.8%) of 1,1,3,3-tetrachloro-2-(trichlorosilyl)-2-methyl-1,3-disilapropane (formula IV); [NMR(CDCl$_3$); δ 5.78 (s, 2H, Si-H), 1.83 (s, 3H, —CH$_3$)], and 0.5 g (0.9%) of 1,1,1,3,3-pentachloro-2-(trichlorosilyl)-2-methyl-1,3-disilapropane (formula V); [NMR(CDCl$_3$); δ 5.82 (s, 1H, Si—H), 2.00 (s, 3H, —CH$_3$)]. 15.9% of 1,1,3,3-tetrachloro-2-methyl-1,3-disilapropane; [NMR (CDCl$_3$); δ 5.62 (s, 2H, Si—H), 1.42–1.39 (d, 3H, —CH$_3$), 1.24–1.18 (m, 1H, —CH=)], 9.3% of 1,1,1,3,3pentachloro-2-methyl-1,3-disilapropane, and 35.5% of trichlorosilane were obtained as by-products. The balance was unidentified substances.

TABLE 5

Mixing Ratio of Chloroform and Alkyl Chloride and the Results

| Entry No. | R'Cl | CHCl$_3$: R'Cl | CHCl$_3$ used (g) | Reaction Time (hr) | Amt. of Products (g) | Composition of Products (%) | | | | |
|---|---|---|---|---|---|---|---|---|---|---|
| | | | | | | III | IV | V | VI | others |
| 24 | t—BuCl | 1:6 | 28.8 | 2.0 | 56.0 | 24.8 | 9.2 | 2.3 | — | 63.7 |
| 25 | n—BuCl | 1:6 | 28.8 | 2.0 | 66.9 | 6.1 | 7.1 | 2.7 | — | 84.1 |
| 26 | i—PrCl | 1:6 | 28.8 | 2.0 | 55.4 | 15.3 | 8.4 | 2.5 | 0.9 | 72.9 |
| 27 | (ClCH$_2$)$_2$ | 1:3:6 | 28.8 | 2.0 | 56.2 | — | 0.6 | 6.1 | 12.3 | 81.0 |

EXAMPLE 7

Reaction of silicon with a mixture of chloroform and alkyl chloride or hydrogen chloride in a fluidized bed The following experiment demonstrates Entry No. 30 of Table 6. 402 g of Si/Cu contact mixture (I-3) prepared in EXAMPLE 2 was charged in a fluidized bed reactor, and dry nitrogen gas was blown into the reactor at the rate of 200 ml/min. After increasing the temperature in the reactor up to 260° C., a 1:6 mixture of chloroform and t-butyl chloride or hydrogen chloride was introduced to the evaporator attached to the bottom of the reactor, while nitrogen was also blown

What is claimed is:

1. Tris(silyl)alkanes represented by formula III

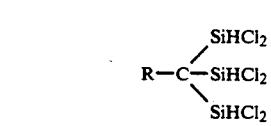

Formula III wherein R represent independently hydrogen or methyl.

2. A method for preparing tris(silyl)alkanes represented by the formula (III), (IV), (V) and (VI) comprising directly reacting a mixture of organic compounds having trichloromethyl groups represented by formula I and hydrogen chloride or alkyl chlorides represented by formula II, with metallic silicon.

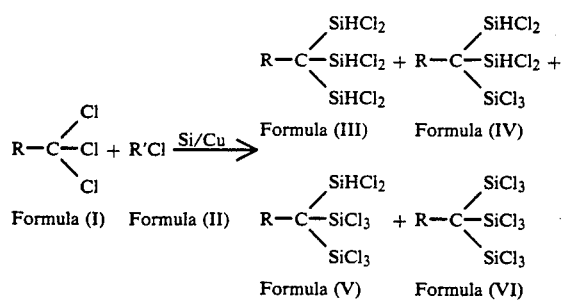

wherein R represent independently hydrogen or methyl and R' represents hydrogen, alkyl($C_1$–$C_4$) or $CH_2CH_2Cl$.

3. The method in accordance with claim 2, wherein R is hydrogen.

4. The method in accordance with claim 2, wherein R is methyl.

5. The method in accordance with claim 2, wherein R' is hydrogen.

6. The method in accordance with claim 2, wherein R' is propyl.

7. The method in accordance with claim 2, wherein R' is n-butyl.

8. The method in accordance with claim 2, wherein R' is n-butyl.

9. The method in accordance with claim 2, wherein R' is chloroethyl.

10. The method in accordance with claim 2, wherein 0.5–12 times of alkyl chloride represented by formula II is added to each mole of trichloromethyl containing organic compound represented by formula I.

11. The method in accordance with claim 2, wherein R'Cl represented by formula II is 1:1 mixture of alkyl chloride and hydrogen chloride.

12. The method in accordance with claim 2, wherein a stirred bed reactor equipped with a spiral band agitator or fluidized bed reactor is used.

13. The method in accordance with claim 2, wherein the pressure of reactor is 1–5 atmospheric pressure.

14. The method in accordance with claim 2, wherein in the reaction 1–15% of micro-spherical acid clay based on the amount of silicon is added.

15. The method in accordance with claim 2, wherein 1–20% of copper or cuprous chloride based on the amount of silicon is added and the range of reaction temperature is from 200° C. to 360° C.

16. The method in accordance with claim 2, wherein 0.01–5% of promoter comprising at least one promoter selected from the group of calcium, titanium, zinc, tin, cadmium, manganese, magnesium, and silver based on the amount of silicon is added as a co-catalyst.

* * * * *

UNITED STATES PATENT AND TRADEMARK OFFICE
CERTIFICATE OF CORRECTION

PATENT NO. : 5,332,849
DATED : JULY 26, 1994
INVENTOR(S) : IL N. JUNG ET AL

It is certified that error appears in the above-indentified patent and that said Letters Patent is hereby corrected as shown below:

Table 5, Entry No. 27, column 3, "1:3:6" should read --1:3.6--.

Column 12, Claim 8, line 4, "n-butyl" should read --t-butyl--.

Signed and Sealed this

Third Day of September, 1996

Attest:

BRUCE LEHMAN

*Attesting Officer*    Commissioner of Patents and Trademarks